United States Patent
Gazzaniga et al.

(10) Patent No.: US 11,135,173 B2
(45) Date of Patent: Oct. 5, 2021

(54) PROLONGED RELEASE PHARMACEUTICAL COMPOSITION COMPRISING CYSTEAMINE OR SALT THEREOF

(71) Applicant: RECORDATI INDUSTRIA CHIMICA E FARMACEUTICA S.P.A., Milan (IT)

(72) Inventors: Andrea Gazzaniga, Santa Giuletta (IT); Matteo Cerea, Grumello del Monte (IT); Alessandra Maroni, Luvinate (IT); Marco Barchielli, Arese (IT)

(73) Assignee: RECORDATI INDUSTRIA CHIMICA E FARMACEUTICA S.P.A., Milan (IT)

( * ) Notice: Subject to any disclaimer, the term of this patent is extended or adjusted under 35 U.S.C. 154(b) by 5 days.

(21) Appl. No.: 16/084,308

(22) PCT Filed: Mar. 14, 2017

(86) PCT No.: PCT/EP2017/055964
§ 371 (c)(1),
(2) Date: Sep. 12, 2018

(87) PCT Pub. No.: WO2017/157922
PCT Pub. Date: Sep. 21, 2017

(65) Prior Publication Data
US 2019/0076368 A1 Mar. 14, 2019

(30) Foreign Application Priority Data
Mar. 18, 2016 (IT) .......................... UA2016A001799

(51) Int. Cl.
*A61K 9/50* (2006.01)
*A61K 31/145* (2006.01)
(52) U.S. Cl.
CPC .......... *A61K 9/5026* (2013.01); *A61K 9/5015* (2013.01); *A61K 9/5042* (2013.01); *A61K 31/145* (2013.01)

(58) Field of Classification Search
CPC .. A61K 9/5026; A61K 9/5021; A61K 9/5042; A61K 9/5047
See application file for complete search history.

(56) References Cited

U.S. PATENT DOCUMENTS

| 8,026,284 B2 | 9/2011 | Dohil et al. | |
| 8,530,523 B2 * | 9/2013 | Tang | A61K 31/13 514/579 |
| 9,173,851 B1 | 11/2015 | Powell et al. | |
| 2005/0004075 A1 * | 1/2005 | Chi | A23K 40/10 514/58 |
| 2009/0285891 A1 * | 11/2009 | Jung | A61K 9/5078 424/484 |
| 2013/0171199 A1 | 7/2013 | Boldhane et al. | |
| 2014/0370085 A1 * | 12/2014 | Powell | A61K 9/5026 424/458 |

FOREIGN PATENT DOCUMENTS

CN 101653426 A 2/2010

OTHER PUBLICATIONS

Thomson Scientific, Database WPI, Week 201021, 2010,2 pages.
International Search Report and Written Opinion for Corresponding International Application No. PCT/EP2017/055964 (11 Pages) (May 29, 2017).

* cited by examiner

*Primary Examiner* — James W Rogers
(74) *Attorney, Agent, or Firm* — Lucas & Mercanti, LLP (57) ABSTRACT

A prolonged release multiple unit dosage form, preferably pellets, of cysteamine, cystamine or a pharmaceutically acceptable salt thereof, preferably cysteamine bitartrate, with a non gastro-resistant coating is described. The dosage form is particularly indicated for the administration to patients once or twice a day and it can be used also for pediatric administration.

14 Claims, 5 Drawing Sheets

PROLONGED RELEASE PHARMACEUTICAL COMPOSITION COMPRISING CYSTEAMINE OR SALT THEREOF

CROSS-REFERENCE TO RELATED APPLICATIONS

This application is a 371 of PCT/EP2017/055964, filed Mar. 14, 2017, which claims the benefit of Italian Patent Application No. UA2016A001799, filed Mar. 18, 2016.

FIELD OF THE INVENTION

The present invention relates to a prolonged release pharmaceutical composition, in particular in the form of multiple units, comprising cysteamine or salts thereof, preferably cysteamine bitartrate.

BACKGROUND OF THE INVENTION

Cysteamine is an active ingredient approved for the treatment of cystinosis.

Cysteamine is the reduced form of cystamine.

Cystinosis is a rare autosomal recessive disease associated with a congenital error of metabolism. In particular, cystinosis is a disease that affects the metabolism of the sulfur amino acid cystine which is obtained by the oxidative reaction between two molecules of cysteine. Due to the malfunctioning of the cystine transport system outside lysosomes, an intralysosomal cystine accumulation occurs.

Cystine accumulates in lysosomes in the form of crystals, which interfere with the functioning of almost all the organs: the first organs to be interested are usually the kidneys and the eyes and subsequently also the liver, bone marrow, rectal mucosa, lymph nodes, thyroid, pancreas and gonads.

There are three clinical forms of cystinosis: infantile or nephropathic, tardive and benign. The infantile or nephropathic cystinosis is the most frequent (about 95% of cases) and severe form of cystinosis. In infantile cystinosis the symptoms appear between the sixth and the eighteenth month of life. The first symptoms to become apparent are anorexia, vomiting, excessive thirst and urination, growth difficulty, rickets and episodes of dehydration.

Infantile cystinosis, if not adequately treated, develops in kidney failure and needs kidney transplant.

Nowadays, the specific treatment of nephropathic cystinosis involves the use of cysteamine bitartrate which is effective in decreasing the cystine intracellular levels, therefore reducing the progression rate of kidney failure in children.

The mechanism of action of cysteamine bitartrate is based on its reaction with cystine to form a mixed disulphide of cysteamine and cysteine. This mixed disulphide is therefore extracted from the cells by the transport system of the amino acid lysine. Therefore, the amount of cystine in the organs is reduced and damages to organs are limited.

For the treatment of nephropathic cystinosis, a medicinal product containing cysteamine bitartrate is known under the brand name CYSTAGON® and takes the form of immediate release capsules 50 and 150 mg (as cysteamine free base), for oral administration 4 times a day.

The need to administrate the drug 4 times a day at regular intervals of 6 hours is a great drawback of the immediate release dosage form since it is uncomfortable to the patient, especially in the pediatric treatment, and it causes hypergastrinemia and consequent gastrointestinal disorders.

Moreover cysteamine is under study for the treatment of others pathologies such as cystic fibrosis, neurodegenerative diseases such as Huntington's disease, malaria and cancer.

The formulation of cysteamine, cystamine or salts thereof, is a technical problem difficult to overcome due to both organoleptic and chemical-physical features of the active ingredient and pharmacokinetic features thereof.

In fact cysteamine is a molecule with an unpleasant smell and taste which is absorbed almost exclusively in the proximal small intestine. Furthermore the dose to be administered for the treatment of cystinosis is high, equal to 1.30 $g/m^2$ a day in patients under 12 years, up to 2 g a day in patients over 12 years or weighing more than 50 kg. Said doses of cysteamine free base correspond to 3.83 $g/m^2$ of bitartrate a day for the pediatric dose and to 5.89 g of bitartrate a day for the adolescent/adult. Recently, in USA and in Europe, the medicinal product PROCYSBI® for the treatment of cystinosis has been put on the market. PROCYSBI® is a gastro-resistant pharmaceutical composition in the form of capsule, containing cysteamine bitartrate in an amount equal to 25 or 75 mg as free base.

This gastro-resistant formulation is disclosed in the patents U.S. Pat. No. 8,026,284 (The Regents of the University of California) and U.S. Pat. No. 9,173,851 (Raptor Pharmaceuticals, Inc.).

According to literature pubblications [Gangoiti et al., British Journal of Clinical Pharmacology, 70(3), 376-382 (2010) and Langman et al., Clin. J. Am. Soc. Nephrol., 7, 1-9 (2012)] the gastro-resistant formulation reduces the side effects linked to gastric irritability and allows to increase the single administered dose and to reduce the frequency of administration to twice a day. On the basis of pharmacokinetic data, however, it can be noted how the gastro-resistant dosage form shows much higher individual values of $C_{max}$ with a prolonged plateau effect compared to an immediate release dosage form. Therefore the gastro-resistant dosage form does not allow to avoid, indeed increases, the side effects linked to the major peak effect of $C_{max}$, such as the excretion of sulphurated compounds through breath and perspiration.

Moreover, in the gastro-resistant dosage form the release onset of the active ingredient depends on pH and therefore depends on the highly variable gastric residence time on the basis of the type of food taken, especially in pediatric administration which needs the simultaneous intake of suitable beverages and/or foods.

Therefore there is still the need of a dosage form of cysteamine administrable twice a day but with a prolonged release which allows to maintain for an adequately long time an effective concentration level of the active ingredient without a peak effect and which guarantees a smaller variability in the release profile.

The technical problem to be solved by the present invention is therefore that of obtaining a cysteamine dosage form which has a good taste-masking effect, guarantees a prolonged adsorption of the active ingredient and allows the administration twice a day without drawbacks linked to peak effects.

SUMMARY OF THE INVENTION

The authors of the present invention have surprisingly found a prolonged release dosage form comprising cysteamine, cystamine or a salt thereof, in particular the bitartrate salt of cysteamine, which overcomes the drawbacks of pharmaceutical forms comprising said active ingredients known in the art.

Therefore an object of the present invention is a prolonged release multiple unit dosage form, preferably in the form of pellets, of cysteamine, cystamine or pharmaceutically acceptable salts thereof having a non gastro-resistant coating.

Said dosage form solves the technical problem illustrated above since it provides a lag time in order to prevent the immediate release of the active ingredient and bioadhesive properties which allow to increase the transit time in the gastro-duodenal tract of maximum absorption of the active ingredient avoiding high peak concentrations.

Multiple unit dosage forms are minitablets, pellets, granulates, crystals, etc.

Preferably the multiple unit dosage form object of the present invention is a pellet dosage form.

The pellets according to the present invention are small free flowing spherical or semi-spherical solid units. They are preferably obtained by extrusion and spheronization according to standard techniques and they consist of a core, essentially made up of the active ingredient and excipients, on which is applied a coating with such a non pH dependent solubility as to obtain a non gastro-resistant dosage form.

The active ingredient is cysteamine or cystamine or a pharmaceutical acceptable salt thereof, preferably cysteamine bitartrate.

Any excipient which provides sufficient spheronization properties of the mixtures can be suitable for the preparation of pellets having a high amount of active ingredient according to the present invention.

Preferably microcrystalline cellulose, starch, hypromellose, crospovidone are used.

A particularly preferred spheronization agent is microcrystalline cellulose.

The relative amount of spheronization agent is computed as weight ratio with the active ingredient. Generally the weight ratio active ingredient:spheronization agent is between 70:30 and 90:10, preferably 80:20.

The 80:20 ratio is the optimum to have a high content of active ingredient and a good physical stability of the dosage form.

Pellets according to the present invention have a particle size between 700 μm and 1400 μm.

An alternative technique for the preparation of pellets is the technique which provide for the layering of the active ingredient in solution, suspension in suitable solvent or suspending liquid vehicles or directly as a powder onto inert material cores such as for example sugar, starch or cellulose derivatives. The realization of a mechanically resistant layer of active ingredient onto cores is made possible by the presence of suitable excipients able to fix the active ingredient on the surface thereof such as povidone, hydroxypropyl cellulose, hypromellose, sugars or any other material with suitable adhesive properties.

Multiple unit pharmaceutical forms, preferably pellets, according to the present invention have a non gastro-resistant coating which is their main characterising feature.

Said coating is made up mainly by a non hydrosoluble material or by a material having a non pH dependant aqueous solubility, optionally in admixture with one or more components selected among plasticizers, non-sticking agents and canalizing agents.

Examples of suitable materials are polyvinyl acetate; ethyl cellulose; cellulose acetate; insoluble acrylic derivatives such as poly(ethyl acrylate-co-methyl methacrylate-co-trimethylammonium ethyl methacrylate chloride) 1:2:0.1 (marketed for example under the name Eudragit® RS), poly(ethyl acrylate-co-methylmethacrylate-co-trimethylammoniumethylmethacrylate chloride) 1:2:0.2 (marketed for example under the name Eudragit® RL), and poly(ethylacrylate-co-methylmethacrylate) 2:1 (marketed for example under the name Eudragit® NE and Eudragit® NM); hydroxypropyl methylcellulose (HPMC, marketed for example under the name Methocel, Colorcon); hydroxypropyl cellulose (marketed for example under the name Klucel, Ashland); hydroxyethyl cellulose (marketed for example under the name Natrosol, Ashland); polyvinyl alcohol (PVA, marketed for example under the name Gohsenol, Harke); polyethylene oxide (PEO, marketed for example under the name Poliox, DOW).

Preferably polyvinyl acetate or ethyl cellulose are used, even more preferably polyvinyl acetate.

If necessary the plasticizer is selected among propylene glycol (PG), triethyl citrate (TEC), acetyl tributyl citrate (ATBC), acetyl triethyl citrate (ATEC), benzyl benzoate, castor oil, chlorobutanol, diacetylated monoglycerides, dibutylsebacate (DBS), diethyl phthalate, glycerine, mannitol, polyethylene glycol (PEG), polyethylene glycol monomethyl ether, pullulan, sorbitol, sorbitol sorbitan solution, triacetin, tributyl citrate (TBC), vitamin E. Preferably propylene glycol is used.

The preferred non-sticking agent is talc.

The canalizing agent is usually selected among hydrosoluble materials compatible with the control polymer such as for example polyvinyl alcohol-polyethylene glycol copolymer, hydroxypropyl methylcellulose, sugars, salts.

Where the coating is made of polyvinyl acetate, for an optimal compatibility it is preferable to use a copolymer of polyvinyl alcohol-polyethylene glycol as canalizing agent (for ex. Kollicoat®IR).

The coating of the dosage form of the present invention is obtained by spraying a homogeneous aqueous dispersion of the non-hydrosoluble or having a non pH-dependent aqueous solubility material and of any additional components.

The dispersion is sprayed for example on the cores obtained by extrusion and spheronization in an amount suitable to obtain coating thicknesses, depending on the selected formulation, between 10 and 150 μm and preferably 15 and 50 μm. Said thicknesses correspond to weight gain values of the cores between 10% and 60% and preferably between 15% and 30%. These thicknesses allow obtaining a coating suitable for the desired release.

The multiple unit dosage forms of the present invention, thanks to their non-gastro-resistant coating having the features illustrated so far, have a release characterized by a lag time of about 15-30 minutes useful to prevent the release during the mixing with food, if necessary, before the administration to patients, especially pediatric ones. The dosage forms, for the same reason, allow also the release of the most of the active ingredient in the proximal small intestine, where the absorption is optimal. The dosage form disclosed allows to modulate the dissolution profile in order to enable the administration of the cysteamine therapeutic dose at 12 hours intervals (twice a day) without side effects linked to high $C_{max}$ of the active ingredient.

Therefore a further object of the present invention is the use of a prolonged multiple unit dosage form of cysteamine, cystamine or a pharmaceutical acceptable salts thereof with a non gastro-resistant coating for the administration twice a day in patients affected by cystinosis, cystic fibrosis or other diseases.

Particularly preferred is the pediatric use of said dosage form.

The features of the pellets dosage form which represents the preferred embodiment according to the present invention are shown in detail in the following examples and figures.

DETAILED DESCRIPTION OF THE INVENTION

In order to better illustrate the present invention without however limiting it and to provide a detailed description of the figures, the following example are now given.

EXAMPLE 1

Preparation of Pellets by Extrusion and Spheronization

3 Batches of 1.5 kg were prepared and for each batch 3 sub-batches of 500 g of powders were set up. The amounts of cysteamine bitartrate and microcrystalline cellulose weighed powders (balance model 440-490, Kern) were mixed and kneaded with distilled water using a benchtop kneading machine (Chef KM001 model, Kenwood).

The extrusion process was performed through a radial extruder (Nica E 140, GEA) equipped with a 1 mm thick die, fitted with round holes of 1 mm diameter. The feeding rate (feeder) was set at 90 rpm while the rotation rate of the extrusion head (impeller) was set at 70 rpm.

The extruded was processed in a spheronizer equipped with a 64 cm diameter knurled plate (Nica S 450, GEA) at 700 rpm. Spheronization times were set at 5 minutes.

Pellets were dried in oven at 40° C. for 48 hours.

Figure 1:
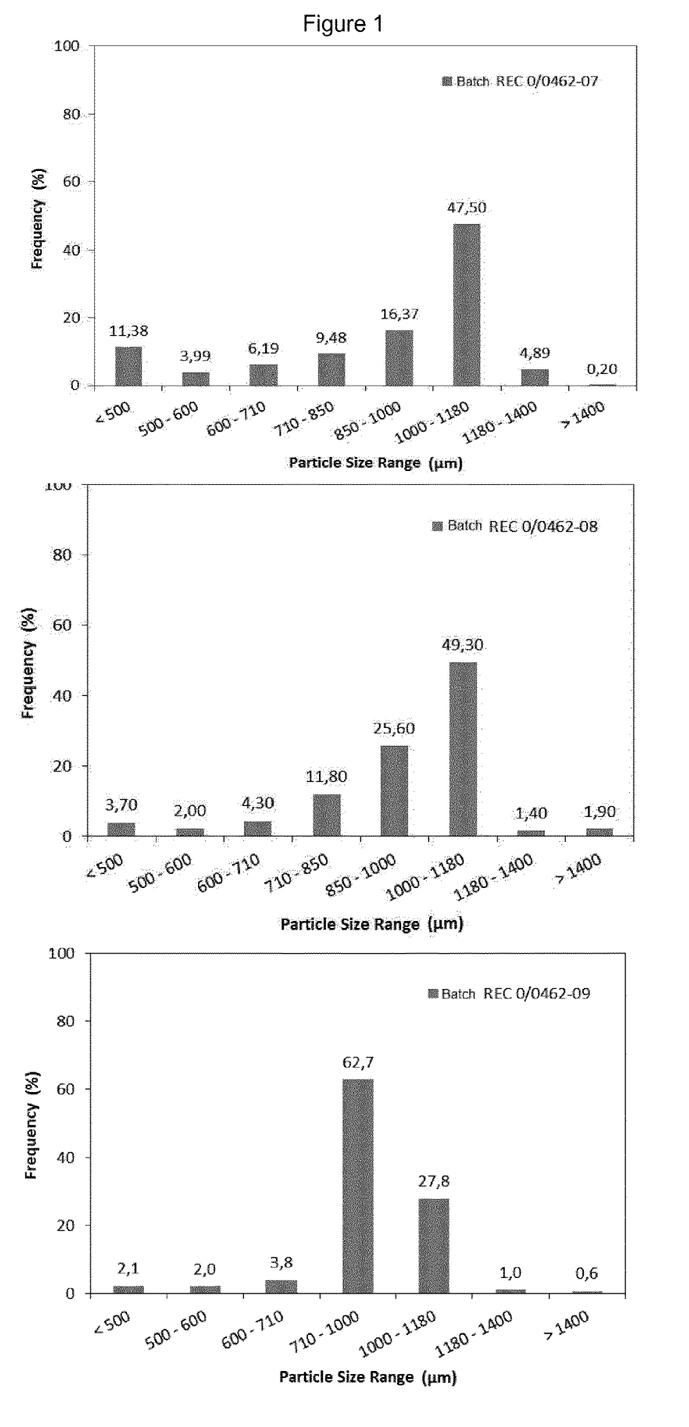
FIG. 1—particle size analysis of non-coated pellets

The particle size analysis of the 3 batches of the resulting non-coated pellets are shown in FIG. 1.

The pellets resulting from the respective sub-batches were mixed before undergoing a sieving process in order to select the product with a particle size between 710 and 1180 μm.

The pellets were packaged in double polyethylene sachet and stored away from light at room temperature; in the external sachet 5 desiccant sachets (Minipack®, 1 g) were added.

The quali-quantitative composition of the resulting pellets is the following:

| Cysteamine | 80% |
|---|---|
| Microcrystalline cellulose | 20% |

Distilled water used for the mixture: 30% compared to the powder weight.

EXAMPLE 2

Pellet Coating with Polyvinyl Acetate Dispersion

Pellet coating was performed operating in a bottom spray fluid bed (GPCG 1.1, Glatt) by spraying aqueous polymeric dispersions of polyvinyl acetate (Kollicoat®SR30D).

In all the coating formulations 10% propylene glycol, computed on the basis of the amount of polyvinyl acetate in the formulation, was used as plasticizer. As canalizing agent a polyvinyl alcohol-polyethylene glycol copolymer (Kollicoat®IR) in proportions of 5%, 7.5% and 10% computed on the basis of the amount of the coating polymer was used.

Polyvinyl Acetate Dispersion

| Kollicoat ® SR30D | 266.5 g (46.84% w/w) |
|---|---|
| Propylene glycol | 8.0 g (1.40% w/w) |
| Talc | 28.0 g (4.92% w/w) |
| Distilled water | 266.5 g (46.84% w/w) |
| Total | 569.0 g (100%) |

Propylene glycol was diluted with 116.5 g of distilled water in a beaker prior to be incorporated to the Kollicoat® SR30D dispersion. The talc was homogenised with the rest of the water (150 ml) in a separate beaker using the ultraturrax (20000 rpm for 3 minutes). The two dispersions were finally blended through magnetic stirring until a homogeneous dispersion was obtained (about 5 minutes). During the coating process the film coating system was maintained under constant stirring with a magnetic stirring bar.

For the coating 500 g of pellets were used.

The coating process parameters are the following:

| Process parameters | heating | spraying | drying |
|---|---|---|---|
| Time (min) | 10 | 90-120 | 10 |
| In air temperature (° C.) | 35 | 39-41 | 38-40 |
| Product temperature (° C.) | 33 | 33-38 | 32-35 |
| Out air temperature (° C.) | | 33-38 | |
| In air volume (m³/h) | | 70 | 70 |
| Product pressure (P) | | 2000 | 2000 |
| Spraying pressure (bar) | | 2.0 | |
| Pump position | | 4-10 | |

Samples of coated product were collected after spraying of about 250 and 500 g of film coating dispersion.

Coated pellets were packaged in double sachet of polyethylene. In the external sachet 5 desiccant sachets (Minipack®, 1 g) were added. Pellets packaged in this way, were stored away from light at room temperature.

Polyvinyl Acetate and Canalizing Agent
Dispersions (Kollicoat® IR)

The following dispersion were prepared:

Dispersion with 5% Kollicoat®IR

| | |
|---|---|
| Kollicoat® SR30D | 266.5 g (46.84% w/w) |
| Propylene glycol | 8.0 g (1.40% w/w) |
| Kollicoat® IR | 4.0 g (0.70% w/w) |
| Talc | 28.0 g (4.92% w/w) |
| Distilled water | 262.5 g (46.14% w/w) |
| Total | 569.0 g (100%) |

Dispersion with 7.5% Kollicoat®IR

| | |
|---|---|
| Kollicoat® SR30D | 266.5 g (46.84% w/w) |
| Propylene glycol | 8.0 g (1.40% w/w) |
| Kollicoat® IR | 6.0 g (1.05% w/w) |
| Talc | 28.0 g (4.92% w/w) |
| Distilled water | 260.5 g (45.78% w/w) |
| Total | 569.0 g (100%) |

Dispersion with 10% Kollicoat®IR

| | |
|---|---|
| Kollicoat® SR30D | 266.5 g (46.84% w/w) |
| Propylene glycol | 8.0 g (1.40% w/w) |
| Kollicoat® IR | 8.0 g (1.40% w/w) |
| Talc | 28.0 g (4.92% w/w) |
| Distilled water | 258.5 g (45.44% w/w) |
| Total | 569.0 g (100%) |

In two separate beakers Kollicoat®IR (80 g of distilled water) and propylene glycol (60 g of distilled water) were dispersed. The preparations were then combined with the Kollicoat®SR30D dispersion by mixing through magnetic stirring. The talc was homogenized with the rest of the water in a separate beaker using the Ultraturrax homogenizer (20000 rpm for 3 min) and added to the polymeric dispersion. The film coating system was maintained under constant magnetic stirring until a homogeneous dispersion was obtained (about 10 minutes).

Pellets were coated in a bottom spray fluid bed (Glatt GmbH, GPCG 1.1 model). For the coating 500 g of pellets were used. Portions of coated product were collected after spraying of 250, 375 and 500 g of dispersion.

Coating process parameters are the following:

| Process parameters | heating | spraying | drying |
|---|---|---|---|
| Time (min) | 10 | 90-120 | 10 |
| In air temperature (° C.) | 35 | 39-41 | 38-40 |
| Product temperature (° C.) | 33 | 33-38 | 32-35 |
| Out air temperature (° C.) | | 33-38 | |
| In air volume (m³/h) | | 70 | |

| Process parameters | heating | spraying | drying |
|---|---|---|---|
| Product pressure (P) | | 2000 | |
| Spraying pressure (bar) | | 2.0 | |
| Pump position | | 4-10 | |

Coated pellets were packaged in a double polyethylene sachet. In the external sachet 5 desiccant sachets (Minipack®, 1 g) were added. Pellets packaged in this way were stored away from light at room temperature.

EXAMPLE 3

Pellet Coating with Polyvinyl Acetate Dispersion

Pellet coating was performed operating in bottom spray fluid bed (GPCG 1.1, Glatt) by spraying aqueous polymeric dispersions of polyvinyl acetate (Kollicoat®SR30D).

Polyvinyl Acetate Dispersions

| | |
|---|---|
| Kollicoat®SR30D | 234.2 g (46.8% w/w) |
| Triethyl citrate | 3.5 g (0.7% w/w) |
| Talc | 24.6 g (4.9% w/w) |
| Distilled water | 237.7 g (47.6% w/w) |
| Total | 500.0 g (100%) |

The weighed amount of triethyl citrate was poured into a beaker containing Kollicoat®SR30D and about 200 g of distilled water maintained under constant stirring. The talc and the rest of the water were mixed in a second beaker and then combined with the polymeric dispersion. The system was maintained under constant stirring until complete dispersion for about 15 minutes.

300 g of pellets 100 g of which containing cysteamine bitartrate (particle size fraction between 710 and 1000 µm) and 200 g of placebo pellets (sugar seed with a particle size of 850-10000 µm) were used as coating substrate.

Coating process parameters are the following:

| Process phase | Heating | Film coating | | | | | | | | Drying |
|---|---|---|---|---|---|---|---|---|---|---|
| Time (min) | 5 | 0 | 10 | 20 | 30 | 40 | 50 | 60 | 80 | 5 |
| In air temp. (° C.) | 40 | 40 | 41 | 43 | 40 | 40 | 41 | 40 | 40 | 40 |
| Product temp. (° C.) | 35 | 35 | 33 | 32 | 32 | 32 | 32 | 32 | 32 | 37 |
| Out air temp. (° C.) | | 34 | 33 | 32 | 32 | 31 | 31 | 31 | 32 | |
| In air volume (m³/h) | | 75 | 80 | 75 | 74 | 77 | 75 | 80 | 75 | |
| Product pressure (P) | | 2768 | 2822 | 2915 | 2832 | 2836 | 2739 | 2812 | 3790 | |
| Spr. Press. (bar) | | 2.0 | 2.0 | 2.0 | 2.0 | 2.0 | 2.0 | 2.0 | 2.0 | |
| Pump posit. | | 5 | 6 | 0 | 6 | 6 | 6 | 6 | 6 | |
| Sprayed amount (g) | | 0 | 52.8 | 125.0 | 172.5 | 236.0 | 292.8 | 356.0 | 472.7 | |

For each batch portions of coated product were collected after nebulization of 125, 250 and 375 g of dispersion.

Coated pellets were packaged in a double polyethylene sachet. In the external sachet 5 desiccant sachets (Minipack®, 1 g) were added. The so packaged pellets were stored away from light at room temperature.

EXAMPLE 4

Pellet Coating with Ethyl Cellulose Dispersion

Pellet coating was performed operating in bottom spray fluid bed (GPCG 1.1, Glatt) by spraying aqueous polymeric dispersions of ethylcellulose with different contents (10% and 15%) of hydroxypropyl methylcellulose (Methocel®5LV).

Ethyl Cellulose Dispersions

| Dispersion with 10% Methocel | |
|---|---|
| Surelease ®E-7-19040 | 216 g (43.2% w/w) |
| Methocel ®5LV | 6 g (1.2% w/w) |
| Distilled water | 278 g (55.6% w/w) |
| Total | 500.0 g (100%) |

| Dispersion with 15% Methocel | |
|---|---|
| Surelease ®E-7-19040 | 204 g (40.8% w/w) |
| Methocel ®5LV | 9 g (1.8% w/w) |
| Distilled water | 287 g (54.4% w/w) |
| Total | 500.0 g (100%) |

The weighed amount of hydroxypropyl methylcellulose was poured a little bit at a time in a beaker containing about 200 g of distilled water and maintained under magnetic stirring until complete dissolution (about 1 hour). To this solution the Surelease® suspension was added always maintaining under stirring and completing the formulation with the remaining intended amount of water.

300 g of pellets 100 g of which containing cysteamine bitartrate (particle size range between 710 and 1000 µm) and 200 g of placebo pellets (sugar seed with a particle size of 850-1000 µm) were used as coating substrate.

Coating process parameters are the following:
Dispersion with 10% Methocel

| Process phase | Heating | Film coating | | | | | | | | Drying |
|---|---|---|---|---|---|---|---|---|---|---|
| Time (min) | 5 | 0 | 10 | 20 | 30 | 40 | 50 | 60 | 80 | 90 | 15 |
| In air temp. (° C.) | 60 | 53 | 60 | 60 | 58 | 60 | 62 | 59 | 61 | 59 | 50 |
| Product temp. (° C.) | | 45 | 43 | 44 | 47 | 45 | 45 | 42 | 44 | 44 | 44 |
| Out air temp. (° C.) | | 46 | 45 | 46 | 48 | 45 | 45 | 43 | 45 | 44 | |
| In air volume (m³/h) | | 64 | 59 | 59 | 61 | 57 | 54 | 59 | 59 | 61 | |
| Product pressure (P) | | 2280 | 1914 | 1967 | 1894 | 1962 | 1652 | 1796 | 1645 | 1577 | |
| Spr. Press. (bar) | | 2.0 | 2.0 | 2.0 | 2.0 | 2.0 | 2.0 | 2.0 | 2.0 | 2.0 | |
| Pump posit. | | 6 | 5 | 5 | 6 | 7 | 8 | 8 | 8 | 8 | |
| Sprayed amount (g) | | 0 | 51.8 | 97.0 | 125.0 | 169.4 | 232.9 | 306.1 | 432.3 | 496.1 | |

Dispersion with 15% Methocel

| Process phase | Heating | Film coating | | | | | | | | Drying |
|---|---|---|---|---|---|---|---|---|---|---|
| Time (min) | 5 | 0 | 10 | 20 | 35 | 45 | 55 | 65 | 75 | 81 | 15 |
| In air temp. (° C.) | 60 | 60 | 60 | 60 | 61 | 61 | 59 | 60 | 60 | 60 | 50 |
| Product temp. (° C.) | 40 | 40 | 42 | 43 | 45 | 44 | 43 | 44 | 43 | 44 | 45 |
| Out air temp. (° C.) | | 40 | 41 | 42 | 44 | 44 | 43 | 44 | 43 | 44 | |
| In air volume (m³/h) | | 56 | 58 | 56 | 62 | 60 | 59 | 5957 | 59 | 61 | |
| Product pressure (P) | | 1909 | 1953 | 1899 | 1933 | 1811 | 1777 | 1671 | 1699 | 1789 | |
| Spr. Press. (bar) | | 2.0 | 2.0 | 0.6 | 2.0 | 2.0 | 2.0 | 2.0 | 2.0 | 2.0 | |
| Pump posit. | | 6 | 6 | 0 | 7 | 7 | 7 | 8 | 7 | 7 | |
| Sprayed amount (g) | | 0 | 68.2 | 125.0 | 208.8 | 169.4 | 334.3 | 395.9 | 463.1 | 496.4 | |

For each batch portions of coated product were collected after spraying 125, 250 and 375 g of dispersion.

The coated pellets were packaged in a double polyethylene sachet. In the external sachet, 5 desiccant sachets (Minipack®, 1g) were added. Pellets packaged in this way were stored away from light at room temperature.

EXAMPLE 5

Release Test

The release test of pellets coated with polymeric dispersion of polyvinyl acetate was performed using a dissolution apparatus according to Pharmacopoeia specifications in the following conditions:

Apparatus: paddle, 100 rpm
Dissolution medium: 500 ml of gastric fluid without enzymes (SGF) (USP) at 37° C.
Samples weight: 190 mg (about 150 mg of cysteamine tartrate)
Sampling times: 0, 15, 30, 60, 90, 120, 180 and 240 minutes At predetermined times 1 ml of fluid was collected from each vessel and filtered (0.45 µm nylon syringe filter Agilent Technologies 9301-0985) before undergoing quantitative analysis by HPLC.

The release test of pellets coated with ethyl cellulose polymeric dispersion was performed using a dissolution apparatus in compliance with Pharmacopoeia specifications in the following conditions:

Apparatus: paddle, 100 rpm
Dissolution medium: 500 ml of gastric fluid without enzymes (SGF) (USP) at 37° C.
Samples weight: 560 mg (about 150 mg of cysteamine tartrate)
Sampling times: 0, 15, 30, 60, 90, 120, 180, 240 and 300 minutes At predetermined times 2 ml of fluid were collected from each vessel by filtering with a 10 µm filter. The collected samples were further filtered with a 0.45 µm filter before undergoing quantitative analysis by HPLC.

Figure 2:
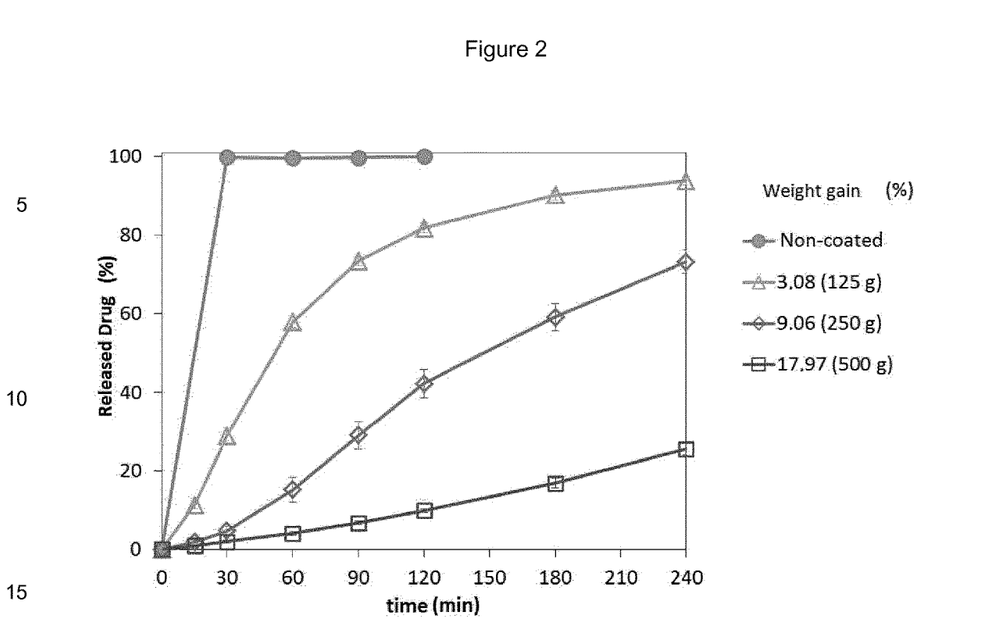
FIG. 2—release profiles of pellets coated with Kollicoat®SR30D and propylene glycol FIG. 3—release profiles of pellets coated with Kollicoat®SR30D, propylene glycol and Kollicoat®IR FIG. 4—release profile of pellets coated with Kollicoat®SR30D, propylene glycol and 5% Kollicoat®IR FIG. 5—release profile of pellets coated with Kollicoat®SR30D, propylene glycol and 7.5% Kollicoat®IR FIG. 6—release profiles of pellets coated with Kollicoat®SR30D, propylene glycol and different proportions of Kollicoat®IR FIG. 7—release profiles of pellets coated with ethylcellulose and 10% HPMC FIG. 8—release profiles of pellets coated with ethylcellulose and 15% HPMC FIG. 9—release profiles of pellets coated with Kollicoat®SR30D and triethyl citrate

The release profiles of pellets coated with Kollicoat®SR30D and propylene glycol as plasticizer are shown in FIG. 2 compared to the release profile of non-coated pellets. Release profiles of pellets coated with increasing amounts (125 g, 250 g, 375 g, 500 g) of sprayed dispersion are shown.

Non-coated pellets show a very rapid release of the active ingredient. In fact, within 30 minutes, the administered dose is completely dissolved.

Pellets coated with 250 and 375 g of formulation show profiles characterized by a short lag-time of about 30 minutes and by a release of the active ingredient slightly lower than 80% within 4 hours.

Figure 3:
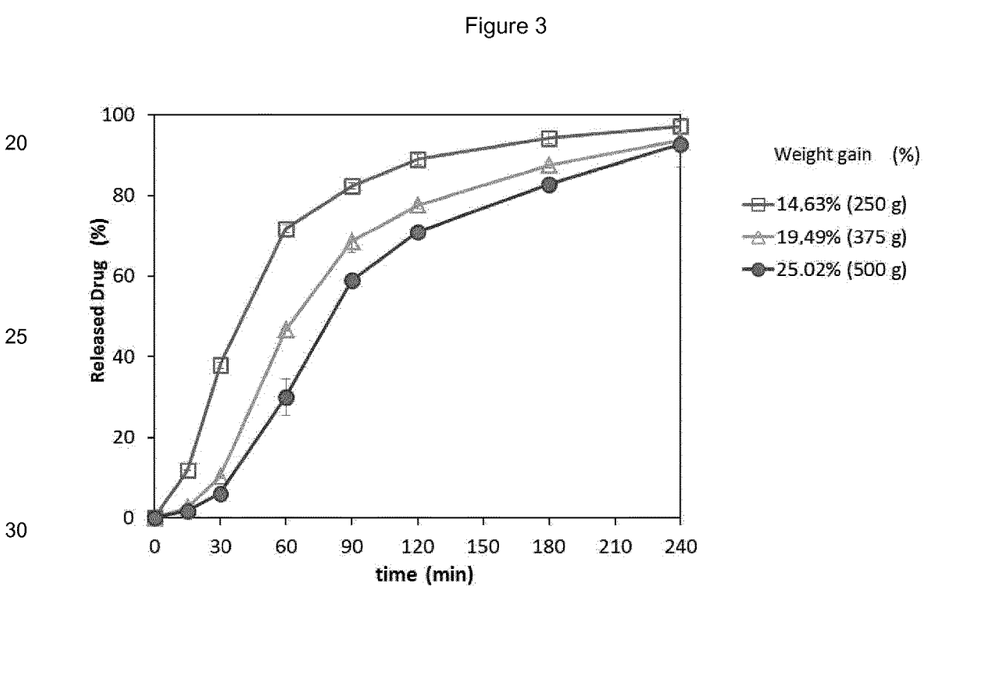

In FIG. 3 the release profiles of pellets coated with increasing amounts of sprayed dispersion containing Kollicoat®SR30D, propylene glycol and Kollicoat®IR are shown.

Pellets coated with the formulation containing 10% Kollicoat®IR, film coating dispersion sprayed and weight gain being equal, show faster release profiles if compared with pellets coated without canalizing agent.

The release profile of pellets coated with 250 g of film coating dispersion does not show lag-time and the dose is completely released within 4 hours. In both cases (for 19.49% and 25.05% of weight gain) a lag-time of about 15 minutes is obtained, with less than 10% of active ingredient released after 30 minutes, after which the active ingredient is almost completely released within 4 hours.

Figure 4:
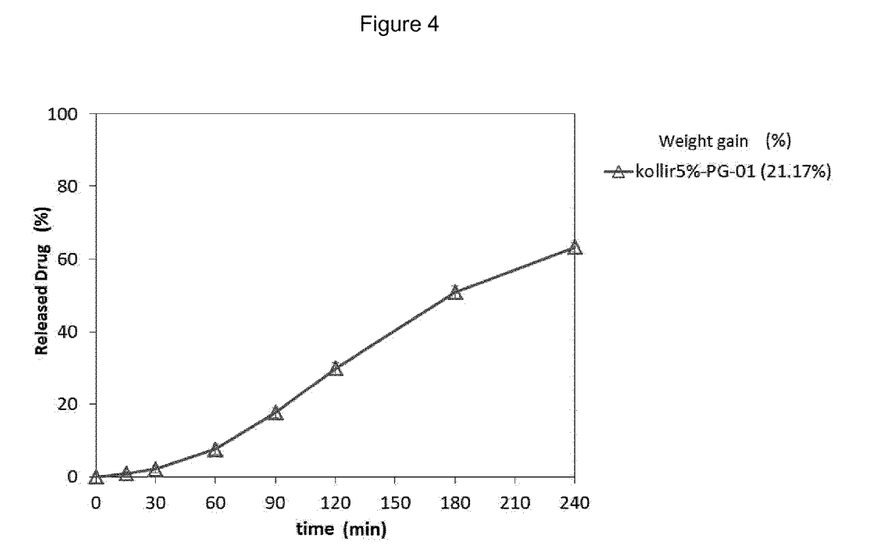

Pellets coated with the film coating dispersion containing 5% of canalizing agent show a release rate of the active ingredient very slow as showed in FIG. 4.

Figure 5:
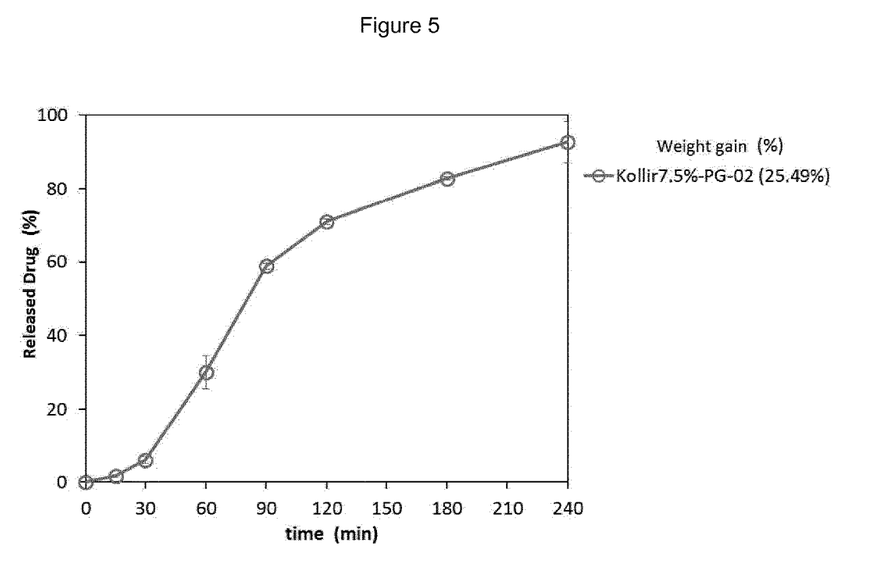

Pellets coated with the film coating dispersion containing 7.5% of canalizing agent show the release profile provided in FIG. 5.

Figure 6:
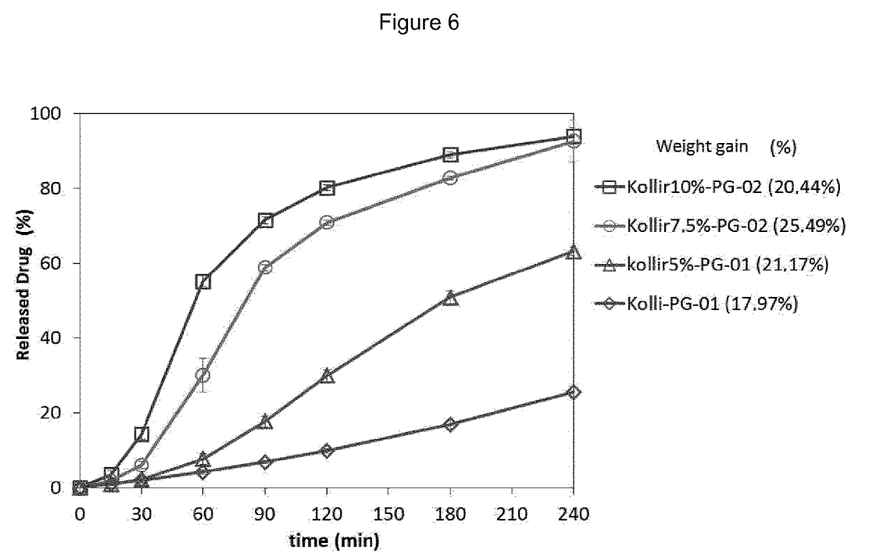
Figure 7:
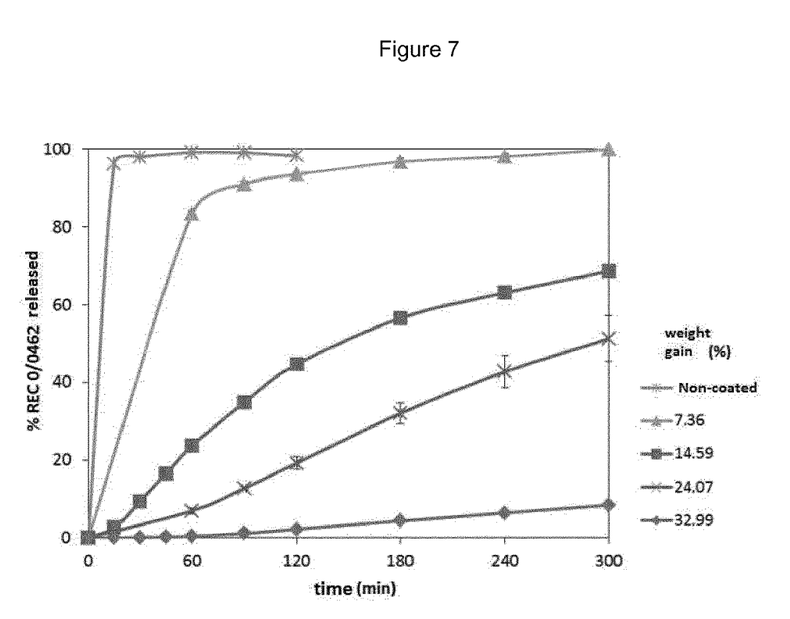
Figure 8:
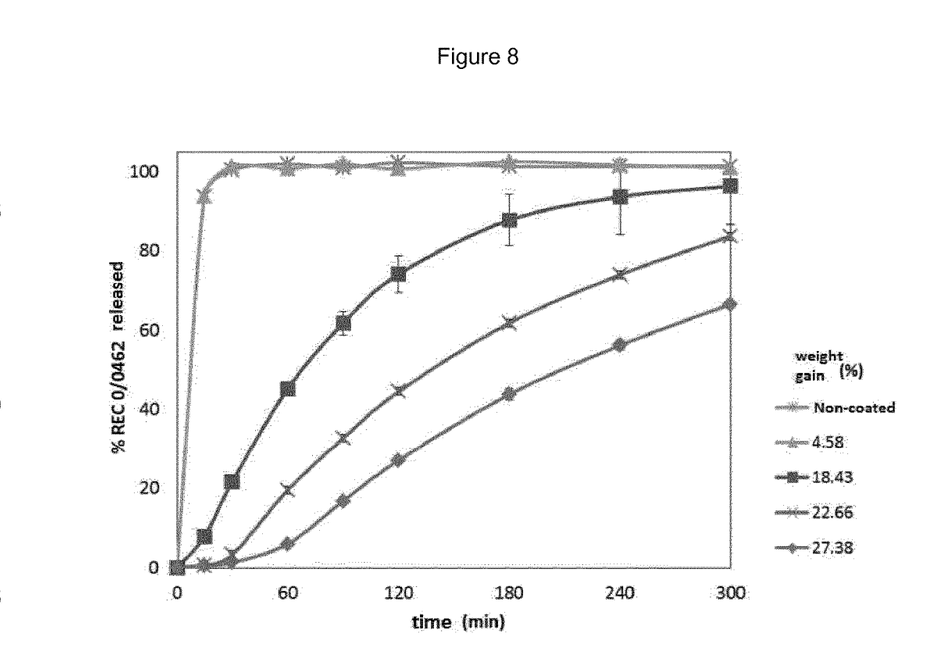
Figure 9:
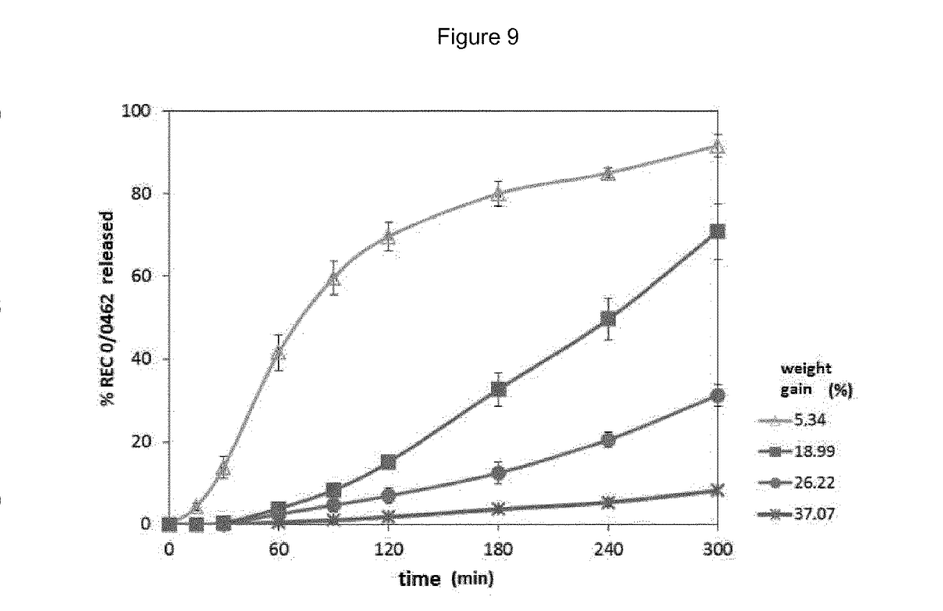

In FIG. 6 is provided a summary graph of the release profiles corresponding to formulations coated without and with different concentrations of canalizing polymer.

EXAMPLE 6

Stability Test

About 1.0 g of pellets for each batch were packaged in blisters or in blisters further sealed in an aluminium sachet.

The blisters packaging was performed by manual blistering machine at 130° C. for 10 seconds (Minipack, Bonapace) using preformed PVC/PE/Aluminium blisters (type C format). The sealing in aluminium sachets was performed by manual thermosealer.

Test Conditions

The packaged samples were stored at a temperature of 40° C. and 75% of relative humidity.

To obtain these conditions, blisters were put into a water-tight glass crystalliser with a saturated NaCl solution at the bottom. The crystalliser was then stored in oven at 40° C.

Sampling times: 0, 1, 3 and 6 months.

Pellets coated with a dispersion of polyvinyl acetate and canalizing agent prepared according to example 2, subject to the accelerated stability test, were found to be stable.

The invention claimed is:

1. A prolonged release dosage form comprising:
a multiple unit dosage form,
each of the multiple units consisting of a pellet with a solid core formed from a mixture of cysteamine bitartrate and a spheronization agent selected from the group consisting of microcrystalline cellulose, starch, hypromellose and crospovidone,
wherein each of the multiple units of the multiple unit dosage form has a non gastro-resistant coating, and
wherein the non gastro-resistant coating consists of a polymer material which is non-hydrosoluble, or has a non pH-dependent aqueous solubility,
wherein the non gastro-resistant coating is optionally in admixture with one or more components selected from the group consisting of plasticizers, non-sticking agents and canalizing agents.

2. The dosage form according to claim 1, wherein the polymer material is selected from the group consisting of polyvinyl acetate; ethylcellulose; cellulose acetate; poly(ethylacrylate-co-methylmethacrylate-co-trimethylammoniumethyl methacrylate chloride) 1:2:0.1, poly(ethylacrylate-co-methylmethacrylate-co-trimethylammoniumethyl methacrylate chloride) 1:2:0.2 and poly(ethylacrylate-co-methylmethacrylate) 2:1; hydroxypropyl methylcellulose; hydroxypropyl cellulose; hydroxyethyl cellulose; polyvinyl alcohol; and polyethylene oxide.

3. The dosage form according to claim 1, wherein the plasticizer is selected from the group consisting of propylene glycol, triethyl citrate, acetyl tributyl citrate, acetyl triethyl citrate, benzyl benzoate, ricin oil, chlorbutanol, diacetyl monoglycerides, dibutyl sebacate, diethyl phthalate, glycerine, mannitol, polyethylene glycol, polyethylene glycol monomethyl ether, pullulan, sorbitol, sorbitol sorbitan solution, triacetin, tributyl citrate, and vitamin E.

4. The dosage form according to claim 1, wherein the canalizing agent is selected from the group consisting of polyvinyl alcohol-polyethylene glycol copolymer and hydroxypropyl methylcellulose.

5. The dosage form according to claim 1, wherein the coating consists of a mixture of polyvinyl acetate, propylene glycol and polyvinyl alcohol-polyethylene glycol copolymer.

6. The dosage form according to claim 1, wherein the coating represents a weight gain of the uncoated multiple units from 10% to 60% by weight.

7. The dosage form according to claim 2, wherein the polymer material is polyvinyl acetate or ethylcellulose.

8. The dosage form according to claim 3, wherein the plasticizer is propylene glycol.

9. The dosage form according to claim 6, wherein the coating represents a weight gain of the uncoated multiple units from 15 to 30% by weight.

10. The dosage form according to claim 1, wherein the cysteamine bitartrate and the spheronization agent are in a weight ratio of 70:30 to 90:10.

11. The dosage form according to claim 1, wherein each pellet has a particle size between 700 µm and 1400 µm.

12. The prolonged release dosage form of claim 1, wherein the cysteamine bitartrate is released from the dosage form in a non-pH dependent manner and without a peak effect.

13. The prolonged release dosage form of claim 1, wherein the non-sticking agent is talc.

14. A prolonged release dosage form comprising:
a multiple unit dosage form,
each of the multiple units being a pellet consisting of a solid core formed from a mixture of cysteamine bitartrate and a spheronization agent being microcrystalline cellulose,
wherein each of the multiple units of the multiple unit dosage form has a non gastro-resistant coating,
wherein the non gastro-resistant coating is in admixture with a plasticizer, a non-sticking agent, and a canalizing agent and,
wherein the non-gastro-resistant coating is polyvinyl acetate, the plasticizer is propylene glycol, the non-sticking agent is talc, and the canalizing agent is a polyvinyl alcohol-polyethylene glycol copolymer.

\* \* \* \* \*